United States Patent [19]

Jacobs

[11] Patent Number: 4,816,436
[45] Date of Patent: Mar. 28, 1989

[54] ANTI-ARTHRITIC USE OF INTERLEUKIN-1 PROTEINS

[75] Inventor: Cindy A. Jacobs, Seattle, Wash.

[73] Assignee: Immunex Corporation, Seattle, Wash.

[21] Appl. No.: 925,773

[22] Filed: Oct. 29, 1986

[51] Int. Cl.$^4$ ............................................. A61K 37/02
[52] U.S. Cl. ........................................ 514/2; 514/8;
514/886; 514/825; 530/351
[58] Field of Search ...................... 514/2, 8, 886, 825;
530/351

[56] References Cited

PUBLICATIONS

Bachwich et al., Biochem. Biophys. Res Comm, 136 (1) 1986, pp. 94–101.
Knudsen et al., J. Immunol 137 (10) 1986, pp. 3189–94.
Mizel et al., J. Immunol. vol. 126, 1981, pp. 834–837.
Kawakami et al., Biochem. Biophys Res. Comm vol. 141, 1986, pp. 482–487.
Matsushima et al., Biochemistry, 25 1986, pp. 3424–3429.
Cameron et al., J. Expe. Med. 162, 1985, pp 790–801.
March et al., "Cloning, Sequence and Expression of Two Distinct Human Interleukin-1 Complementary DNAs," Nature 315:641 (1985).
Oppenheim et al., "There is More Than One Interleukin-1," Immunol. Today 7:45 (1986).
Durum et al., "Interleukin 1: An Immunological Perspective," Ann. Rev. Immunol. 3:263 (1985).
Mizel et al., "Stimulation of Rheumatoid Synovial Cell Collagenase and Prostaglandin Production by Partially Purified Lymphocyte-Activating Factor (Interleukin 1)," Proc. Natl. Acad. Sci. 78:2474 (1981).
Postlethwaite et al., "Interleukin 1 Stimulation of Collagenase Productioln by Cultured Fibroblasts," J. Exp. Med. 157:801 (1983).
Dayer et al., "Induction of Human Interleukin 1 mRNA Measured by Collagenase-and Prostaglandin $E_2$-Stimulating Activity in Rheumatoid Synovial Cells," Eur. J. Immunol. 14:898 (1984).
Van Den Berg et al., "Antigen Handling in Antigen-Induced Arthritis in Mice," Am. J. Path. 108:9 (1982).
Crowle et al., "Preferential Development by Mice of Delayed Hypersensitivity to Purified Basic Proteins," J. Allergy 42:140 (1968).
Cooke et al., "The Pathogenesis of Chronic Inflammation in Experimental Antigen-Induced Arthritis," J. Exp. Med. 135:323 (1972).

Primary Examiner—Johnnie R. Brown
Assistant Examiner—Garnette D. Draper
Attorney, Agent, or Firm—Scott G. Hallquist

[57] ABSTRACT

Processes for use of interleukin-1 as an anti-arthritic agent are disclosed, comprising administration of an effective quantity of interleukin-1 (IL-1) in association with a pharmaceutical carrier, to an animal, including man.

9 Claims, 1 Drawing Sheet

ANTI-ARTHRITIC USE OF INTERLEUKIN-1 PROTEINS

BACKGROUND OF THE INVENTION

The present invention relates generally to lymphokines, and particularly to use of certain lymphokines to alleviate inflammation associated with arthritis.

Rheumatoid arthritis is a systemic autoimmune disease of unknown cause, manifested as a chronic inflammation of synovial membranes. This chronic inflammation ultimately results in destruction of connective tissue surrounding the joints. The disease strikes between 1 and 3 percent of all North Americans and Europeans.

The present invention resides in the unexpected discovery that human interleukin-1 proteins are capable of alleviating experimentally induced intra-articular inflammation resembling the chronic synovitis of human rheumatoid arthritis. This discovery was facilitated by recent inventions which enabled production of useful quantities of substantially homogeneous recombinant human IL-1.

Interleukin-1 (IL-1) activity is attributable to proteins released by macrophages and other cell types in response to immunogenic stimulation. This family of proteins has been associated with a complex spectrum of biological activities. IL-1 is a primary immunostimulatory signal capable of inducing thymocyte proliferation via induction of interleukin-2 release, and stimulating proliferation and maturation of B-lymphocytes. In addition, IL-1 has been linked with prostaglandin production and induction of fever, and with promotion of wound healing. Reviews of the literature relating to IL-1 include Oppenheim et al., *Immunol. Today* 7:45 (1986), and Durum et al., *Ann. Rev. Immunol.* 3:263 (1985).

SUMMARY OF THE INVENTION

The present invention provides a process for use of interleukin-1 as an anti-arthritic agent, comprising administration of an effective quantity of interleukin-1 (IL-1) in association with a pharmaceutical carrier, to a mammal, including man.

DETAILS OF THE INVENTION

Figure 1:
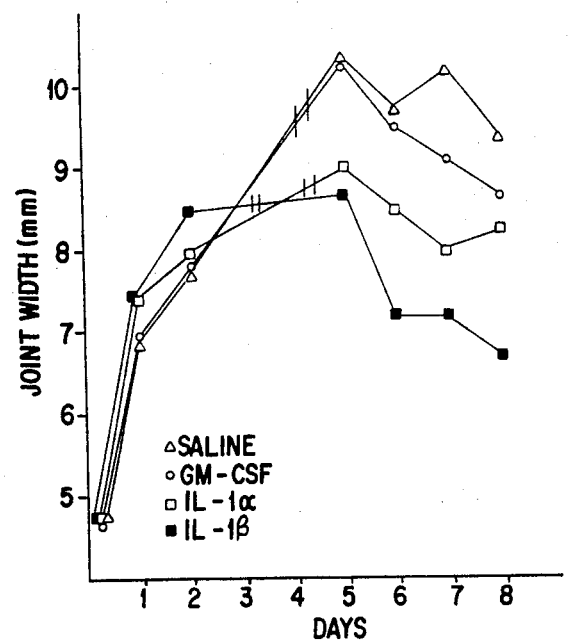
FIG. 1 is a graph showing the post-treatment effects of intra-articular injections of IL-1α and IL-1β upon joint inflammation induced by intra-articular injections of methylated bovine serum albumin (mBSA) in mBSA-immune rats.

Human IL-1 activity resides in two distantly related proteins, herein designated IL-1α and IL-1β (March et al., *Nature* 315:641 (1985)). Both molecules are normally synthesized as larger precursors having molecular weights of about 30,000 daltons, which are subsequently proteolytically processed to yield mature forms having molecular weights of approximately 17,500 daltons. However, unlike IL-1α, the larger precursor of IL-1β is not biologically active prior to proteolytic cleavage to its mature form. All active forms of IL-1α and IL-1β are useful in the treatment methods of the present invention.

As used herein, "interleukin-1" and "IL-1" refer collectively to natural and recombinant forms of human IL-1α and IL-1β. In addition, the term comprehends proteins having amino acid sequences substantially identical to the native forms of human IL-1α and human IL-1β, which exhibit anti-inflammatory or anti-arthritic activity similar to that of native forms. As used herein, the terms "recombinant interleukin-1", and "rIL-1" refer collectively to recombinant forms of human IL-1α and IL-1β produced by microbial fermentation processes.

Substantial identity of amino acid sequences means that the sequences are identical or differ by one or more amino acid alternations (deletions, additions, or substitutions) that do not cause an adverse functional dissimilarity between the synthetic protein and the native form.

Preparation of IL-1

Recently, cDNAs coding for both human IL-1 species were cloned and expressed in microorganisms. This achievement should enable production of sufficient quantities of Il-1α and IL-1β to permit therapeutic use. IL-1 proteins were first purified from cultures of peripheral blood leukocytes substantially as disclosed in copending U.S. patent application Ser. No. 676,533, which is expressly incorporated by reference.

Recombinant human IL-1 species can be extracted from microbial cells under acid conditions. Acid extraction simultaneously solubilizes the IL-1 and precipitates the bulk of the microbial proteins, enabling recovery of IL-1 in supernatants of the acid extracts. Acid-mediated extraction avoids denaturing extractants, and allows purification to proceed directly from the initial extraction step to subsequent ion exchange procedures without solvent interference or protein denaturation. 1. Assays for IL-1 Activity and Endotoxin Levels Progress of rIL-1α or rIL-1β purification can be monitored by a thymocyte mitogenesis assay, which involves ascertaining the capacity of a sample to induce proliferation of thymocytes from CD-1 mice. In this assay, approximately $1 \times 10^6$ thymocytes, obtained from 10 to 12 week old CD-1 mice (Charles River Breeding Laboratories, Wilmington, Mass.) are seeded in round bottom microplate wells (Corning Plastics, Corning, N.Y. in the presence of three-fold serial dilutions of the IL-1 containing fluid samples. The thymocytes are cultured in 150 82 1 of Eagle's minimal essential medium (MEM) containing 50 U/ml penicillin, 50 μg/ml streptomycin, 2 mM glutamine, 0.2 mM gentamycin, 10 mM HEPES (N-2-Hydroxyethylpiperazine-N'-2-ethanesulfonic acid) buffer, pH 7.4, together with 4% w/v human serum and $10^{-5}$ M 2-mercaptoethanol. The samples are cultured for 72 hours at 37° C. in an atmosphere of 5% $CO_2$ in air. Thereafter, the cultures are pulsed for approximately 4 hours with 0.5 microcuries (μCi) of tritiated thymidine ($^3$H-Tdr) after which the cultures are harvested onto glass fiber filter strips with the aid of a multiple-automated sample harvester. Details of this procedure are provided by Gillis et al., *J. Immun.* 120:2027 (1978) and in U.S. Pat. No. 4,411,992.

In this assay, only the CD-1 cells cultured in the presence of IL-1 incorporate $^3$H-Tdr in a dose-dependent manner. CD-1 cells cultured in the absence of IL-1 incorporate only background levels of radiolabel. IL-1 activity is calculated from the linear portion of the $^3$H-Tdr incorporation data. Units of IL-1 activity are determined as the reciprocal dilution of a sample which generates 50% of maximal thymocyte $^3$H-Tdr incorporation as compared to a laboratory standard.

Alternatively, IL-1 activity can be assayed by an IL-1 conversion assay, which relies upon the discovery that IL-1 converts an IL-2 nonproducer cell line, the murine tumor cell line LBRM-33-1A5, to an IL-2 producer. In this assay, LBRM-33-1A5 cells, (ATCC No. CRL-8079) are inactivated by addition of 50 μg/ml mitomycin C and incubated for one hour at 37° C. 100 μl of the inactivated cells (5×10$_5$ cells/ml) are cultured in 96-well flat-bottomed plates in the presence of an equal volume of the mitogen, phytohemagglutinin (PHA, 1%) together with serial dilutions of samples. At hourly time intervals the existence of IL-2 activity generated by IL-1 triggered, mitomycin C-inhibited LBRM-33-1A5 cells is directly ascertained by adding 50 μl of IL-2 dependent CTLL-2 cells (8×10$^4$ cells/ml). The microwell cultures are then incubated for 20 additional hours followed by a 4 hour pulse with 0.5 μCi of $^3$H-Tdr, and the resulting pulsed cultures assayed for thymidine incorporation as detailed above. Only the CTLL-2 cells added to wells previously contacted with IL-1 (thereby inducing IL-2 production in the inactivated LBRM cells) will incorporate radiolabel. This conversion assay is both more rapid and more sensitive than the thymocyte mitogenesis assay.

Protein concentrations can be determined by any suitable method. However, the Bio-rad total protein assay (Bio-rad Laboratories, Richmond, Calif., USA) is preferred. SDS-PAGE can also be employed to monitor purification progress, substantially as described by Kronheim et al., J. Exp. Med. 161:490 (1985) or other suitable technique. Additional details regarding use of the IL-1 assays described above are disclosed by Conlon, J. Immun. 131:1280 (1983) and Kronheim et al., supra.

Endotoxin levels are conveniently assayed using a commercial kit available from Whittaker Bioproducts, Walkersville, Md., U.S.A., (Quantitative Chromogenic LAL QCL-1000) or its equivalent. This method uses a modified limulus amebocyte lysate and synthetic color-producing substrate to detect endotoxin chromogenically. Purified rIL-1α and rIL-1β are tested for presence of endotoxin at multiple dilutions. The assay is preferably performed shortly following completion of purification and prior to storage at −70° C. To minimize the possibility of bacterial contamination during the purification process itself, sterile buffers should be employed.

2. Construction of bacterial expression vectors

Mature IL-1α and IL-1β can be expressed in *E. coli* under the control of the phage λ PL promoter and cI857ts thermolabile repressor. Expression plasmids for rIL-1α and rIL-1β production can be constructed from plasmid pPLc28 (ATCC 53082), plasmid pKK223-3 (available commercially from Pharmacia Fine Chemicals, Uppsala, Sweden) and plasmids containing IL-1α clone 10A (March et al., supra; ATCC 39997) and IL-1β clone IL-1-14 (ATCC 39925) as follows.

To create an expression vector for IL-1α, a 3′ portion of the IL-1α gene, extending from Ser$^{113}$ (nucleotides 337–339) to Ala$^{271}$ (nucleotides 811–813) is inserted into expression vector pPLc28. This is achieved by excising a 499 base pair AluI-NdeI fragment from the 10A clone, to which the following synthetic oligonucleotide linker is joined:

```
AATTCTAGGATAATTA ATG TCA GCA CCT TTT AG
    GATCCTATTAAT TAC AGT CGT GGA AAA TC
```

This linker includes AluI and EcoRI termini, a ribosome binding site, and ATG initiation codon in addition to the IL-1α Ser$^{113}$-Ser$^{117}$ sequence. pPLc28 is then digested to completion with EcoRI and NdeI, and the resulting larger fragment isolated by agarose gel electrophoresis. The linker, 10A clone, and plasmid fragments are then fused using T4 ligase, to provide an expression plasmid herein denoted pILPα. Additional details of the construction of pILPα can be found in the disclosure of copending, commonly assigned U.S. patent application Ser. No. 721,765, the disclosure of which is incorporated by reference herein.

The resulting construct is then employed to transform *E. coli* strain ΔH1 (ATCC 33767; Castellazi et al., *Molec. gen. Genet.* 117:211) to ampicillin resistance, using standard techniques. To express the plasmid-borne IL-1α gene, cultures of transformed ΔH1 are grown in L-broth without ampicillin. When the cultures reach an A$_{720}$ of about 0.5, the culture temperature is raised to about 42° C. to promote derepression of the thermolabile PL promoter. After one hour at elevated temperature, cells are harvested by centrifugation and flash-frozen in a dry-ice/methanol mixture. IL-1α activity in cell extracts can be assayed by either the thymocyte mitogenesis or IL-1 conversion assays previously described. Details regarding purification procedures are provided below.

rIL-1β can be produced via construction of a plasmid, herein designated pILPβ. This vector is assembled from pILPc (March et al., supra), which is constructed by replacing the BamHI/EcoRI fragment of pKK223-3 with a Sau3A/EcoRI fragment from pPLc28 containing the λ PL promoter. This plasmid is digested to completion with EcoRI and PstI, and the largest fragment then ligated to a (1) a 669 base pair HpaII/PstI fragment from pIL-1-14 (ATCC 39925) containing the human IL-1β gene (Ala$^{117}$ to COOH terminus encodes active protein) and (2) the following EcoRI/HpaI synthetic oligonucleotide:

```
AATTCTAGGATAATTA ATG GCA CCT GTA CGA TCA CTG AAC TGC ACG CTC
    GATCCTATTAAT TAC CGT GGA CAT GCT AGT GAC TTG ACG TGC GAG GC
```

Plasmid pILPβ is then used to transform *E. coli* H1 or other cells containing a thermolabile repressor of PL transcription. Following growth to A$_{720}$ of about 0.5, expression of the rIL-1β gene is obtained by heat induction as previously described. rIL-1β activity, as in the case of rIL-1α, can be identified using the thymocyte mitogenesis or IL-1conversion assays cited above.

3. Protein Purification

The general purification scheme described below involves an initial acid extraction from cell pellets, followed by an SPS (Sulphopropyl Sephadex; Pharmacia) column chromatography step and elution from a DEAE-Sephacel (Pharmacia) column. Column fractions containing rIL-1α are then applied to Phenyl Sepharose CL-4B (Pharmacia), while those containing rIL-1β are applied to a Procion Red agarose (Bethesda Research Laboratories) column for final purification.

Sterile buffers are used throughout the purification protocol to safeguard the product from contamination by endotoxin. Chromatography fractions are monitored for protein concentration by the Bio-rad total protein assay (Bio-rad Laboratories, Richmond, Calif., USA) and the progress of purification evaluated by SDS-PAGE as described by Kronheim, J. Exp. Med. *161:490* (1985). IL-1 activity of column fractions is determined by the IL-1 assays previously referenced.

Experiments in which the pH of the initial extraction buffer was varied have indicated that extraction of rIL-1α from *E. coli* cell suspensions at pH 2.8 results in precipitation of significant quantities of contaminating proteins while enabling good recovery of rIL-1α. Similar experiments involving rIL-1β indicate that pH 3.9 is optimal for precipitating unwanted proteins while solubilizing rIL-1β. The optimal pH for the initial extraction step may vary between fermenter batches. For this reason, small-scale pilot runs may be employed to determine optimal pH, particularly where large quantities of material are involved.

rIL-1α and rIL-1β are produced by growth and derepression of appropriate *E. coli* cells harboring high level thermolabile expression plasmids for rIL-1α and rIL-1β. Cells are grown, for example, in a 10 liter fermenter employing conditions of maximum aeration and vigorous agitation. An antifoaming agent (Antifoam A) is preferably employed. Cultures are grown at 30° C. in the super induction medium disclosed by Mott et al., *Proc. Natl. Acad. Sci.* USA 82:88 (1985) plus antibiotics, derepressed at a cell density corresponding to $A_{600}=0.05$ by elevating the temperature to 42° C., and harvested 16 hours after the upward temperature shift. The cell mass is initially concentrated by filtration or other means, then centrifuged at 10,000× g for 10 minutes at 4° C. followed by rapid freezing of the cell pellet.

To achieve the initial acid extraction, cell pellets are suspended in 30 mM Tris-HCl buffer, pH 8, containing 5 mM EDTA and 1 mM phenylmethylsulfonyl fluoride (PMSF). The resulting suspension is rapidly frozen in a dry ice/methanol bath and then thawed. Next, 30 mM sodium citrate buffer at pH 2.8 (rIL-1α) or 3.9 (rIL-1β), containing 5 mM EDTA and 250 μg/ml lysozyme is added to the suspensions. The resulting acid suspensions are incubated for 60 minutes in a 37° C. water bath. Following incubation, the extracts are rapidly frozen in a dry-ice/methanol bath, thawed, and then centrifuged at 4° C. for 45 minutes at 38,000×g. Supernatants are then decanted for use in the next purification step.

Extraction of rIL-1α from the E. coli cell suspension at pH 2.8 results in precipitation of most of the contaminating proteins and good recovery of rIL-1α. The extract is applied to an SPS C-25 column at pH 4. The column can be preconditioned with 0.1% Triton X-100 (polyoxyethylene ether; Sigma Chemical Company, St. Louis, Mo., USA) and 10% fetal calf serum to reduce nonspecific absorption of IL-1 activity to the resin. The columns are washed with 10 mM 2-(N-morpholino)ethanesulfonic acid (MES) buffer, pH 5.0, and protein elutes from the column with 10 mM Tris-HCl, pH 8.1.

Fractions containing IL-1 activity from the previous step are combined and applied to a suitable column containing DEAE-Sephacel previously equilibrated with 10 mM Tris-HCl pH 8.1. Since rIL-1α elutes from the SPS column in the equilibration buffer of the DEAE column, the SPS pool of active fractions can be loaded directly onto the DEAE column, avoiding loss of activity by dialysis. The DEAE column is then washed thoroughly with the starting buffer, and then eluted with a linear gradient of 0 to 600 mM Nacl in 10 M Tris-HCl, pH 8.1, in a total of two column volumes. rIL-1α elutes from the column at 0.17–0.22 Nacl. Most contaminating proteins are eliminated in this step, either by allotting earlier in the salt gradient or remaining bound to the gel after elution of rIL-1α.

Fractions containing rIL-1α are then pooled and treated by addition of sufficient solid ammonium sulfate to provide a final concentration of 0.5 M. The resulting solution is then applied to a 30×2.5 cm column containing Phenyl Sepharose CL-4B, equilibrated with 10 mM Tris-HCl buffer, also 0.5 M in ammonium sulfate, at pH 8.1. The column is washed with starting buffer, and eluted with a decreasing linear gradient of ammonium sulfate starting at 0.5 M and ending at 0 M in about 3 column volumes. Finally, the column is eluted with about 100 ml 10 mM Tris-HCl, pH 8.1. rIL-1α elutes at about 0.25–0.10 M ammonium sulfate. Those fractions containing rIL-1α are pooled and concentrated by reapplication to SPS C-25 as described by Kronheim et al., supra. rIL-1α is eluted using 10 mM phosphate buffered saline (PBS) at pH 8.2. Purified rIL-1α exhibits a specific activity of about $6.5 \times 10^8$ units per mg.

Extraction of rIL-1β from *E. coli* cell suspensions at pH 3.9 results in precipitation of most contaminating proteins and significant recovery of rIL-1β activity. Extracts containing rIL-1β are applied to an SPS C-25 column pretreated with 0.1% Triton X-100 (polyoxyethylene ether; Sigma Chemical Company, St. Louis, Mo., USA) and 10% fetal calf serum. Protein is applied and eluted substantially as described for rIL-1α, above.

Fractions containing IL-1 activity from the SPS step are combined and applied to columns containing DEAE-Sephacel previously equilibrated with 10 mM Tris-HCl pH 8.1. As described for rIL-1α, above, the DEAE columns are washed with the starting buffer and then eluted with linear gradients of 0 to 400 mM NaCl in a total of two column volumes. rIL-1β elutes from the DEAE column at 0.075 M to 0.155 M NaCl.

Fractions containing rIL-1β resulting from the DEAE column step are diluted 1:4 in 10 mM Tris-HCl buffer, pH 8.1, to reduce ionic strength to less than 40 mM, then applied to a 20×2.5 cm column containing Procion Red agarose previously equilibrated with 10 mM Tris-HCl buffer, pH 8.1. The column is washed with starting buffer, and then eluted with a linear gradient in five column volumes ranging from 0 to 1 M NaCl in 10 mM Tris-HCl buffer, pH 8.1. Fractions of 10 ml are collected, analyzed, and then concentrated as described for rIL-1α, above. rIL-1β elutes from the Procion Red column at 0.36-0.46 M NaCl. Purified rIL-1β exhibits a specific activity of about 1.95 x $10^8$ units per mg.

4. Administration of IL-1

In practicing the process of the present invention, purified IL-1 is administered to a mammal in need of anti-arthritic treatment at a therapeutically effective dosage level. The lowest effective dosage levels are determined by initiating treatment at higher dosage levels and reducing the amounts of IL-1 administered until relief from inflammation is no longer achieved. Generally, therapeutic dosages will range from about 10,000 to 100,000,000 units IL-1 activity per kg body weight.

Injection offers the most practical method of administration, either intra-articularly, intramuscularly, intravenously, or intraperitoneally. Typically, IL-1 proteins will be administered in the form of compositions comprising purified protein in conjunction with physiologically acceptable carriers or diluents. Neutral buffered saline or saline mixed with conspecific serum albumin are exemplary appropriate diluents. Preferably, conspecific forms of IL-1 are employed.

Chronic synovitis can be experimentally induced by intra-articular (IA) injection of soluble proteins, e.g., egg albumin or bovine serum albumin, in mammals previously rendered immune to the injected protein. The resulting sustained local immune response is apparently maintained by slow release of antigen retained in the injected joints. Due to similarities in histological characteristics and chronicity, antigen-induced arthritis (AIA) in animals has been used as an experimental model for human rheumatoid arthritis.

The following examples illustrate use of IL-1α and IL-1β to ameliorate joint inflammation experimentally induced in immune rats by intra-articular injection of antigen.

EXAMPLE 1

Intra-articular Administration of IL-1α and IL-1β Prior to Induction of Antigen-Induced Arthritis 14 rats were divided into four groups, designated Groups A, B, C, and D. Groups A and B, each containing four rats, were immunized by subcutaneous injections of methylated bovine serum albumin (mBSA). For each immunization, 1 mg mBSA was emulsified in complete Freunds adjuvant (CFA) in a volume of 0.4 ml, and injected in 0.2 ml doses into two flank sites. Group C, containing four rats, and Group D, containing two rats, were injected at two flank sites with 0.2 ml neutral saline solution emulsified in CFA.

Using a 30-gauge needle on a tuberculin syringe and a Tridak stepper set at a 0 µl volume, the right hind knee joints of Group A individuals were injected intra-articularly (IA) with 100 ng IL-1β on days 1, 7 and 14 following immunization with mBSA. On the same days, individuals in Group B received right hind knee joint IA injections of 100 ng IL-1α; Group C received 100 ng IL-1β; and Group D received saline. At the same time, the left hind knee joints of Groups A, B and D were injected with saline, and Group C with IL-1α.

On day 21, both right and left hind knee joints of rats in Groups A and B were injected with 100 µg mBSA in a 10 µl volume, while Groups C and D received bilateral IA saline injections.

The diameter of the largest region of the treated joints was measured using a caliper. The results obtained, expressed as means ± SEM, are set forth in Table 1, below:

TABLE 1

Joint Inflamation Induced by Intra-Articular Antigen Following Treatment with IL-1α and IL-1β (Joint Diameter in mm)

| Days After AIA | Pretreatment | | |
|---|---|---|---|
| | IL-1α | IL-1β | Saline |
| 0 | 5.1 ± .1 | 5.8 ± .1 | 5.4 ± .1 |
| 1 | 10.7 ± .3 | 10.7 ± .5 | 10.2 ± .3 |
| 2 | 9.2 ± .4 | 9.2 ± .4 | 8.8 ± .3 |
| 5 | 9.1 ± .4 | 8.1 ± .4 | 9.5 ± .3 |
| 7 | 8.6 ± .6 | 7.6 ± .5 | 9.7 ± .3 |
| 8 | 7.5 ± .6 | 6.7 ± .3 | 8.8 ± .5 |

The foregoing measurements indicate a correlation of reduced joint inflammation with IL-1α and IL-1β pretreatment in days 5-8 following intra-articular injection of antigen.

EXAMPLE 2

Intra-articular Administration of IL-1α and IL-1β Before and After Induction of Antigen-Induced Arthritis 20 rats were equally divided into four groups, designated Groups E through H. All rats were immunized with mBSA as described in Example 1, above. On days 1, 7, and 14 following immunization, Group E rats received right hind knee joint IA injections of 100 ng IL-1β; Group F rats received right hind knee joint IA injections of 100 ng IL-1α. Group E rats received left hind knee joint IA injections of 100 ng murine granulocyte-macrophage colony stimulating factor (MuGM-CSF) and Group F received IA saline at the same intervals.

On Day 21, all 20 rats were injected IA with 100 µg mBSA in both hind knee joints. On Day 22, Group G rats were injected in the right hind knee joint with 100 ng IL-1β, and in the left hind knee joint with 100 ng GM-CSF. Group H rats received 100 ng IL-1α (right) and saline (left). Groups E and F were left untreated during this time period.

The diameter of the widest region of the hind knee joint region was then measured as described above. Results are set forth in FIG. 1, and in Tables 2 and 3, below:

TABLE 2

Joint Inflammation Induced by Intra-Articular Antigen Following Treatment with IL-1α and IL-1β (Joint Diameter in mm)

| Days After AIA | Pretreatment | | | |
|---|---|---|---|---|
| | IL-1α | IL-1β | Saline | GM-CSF |
| 0 | 5.5 ± .2 | 5.3 ± .1 | 4.7 ± .1 | 4.7 ± .1 |
| 1 | 7.5 ± .1 | 7.6 ± .2 | 7.4 ± .3 | 7.0 ± .2 |
| 2 | 8.6 ± .2 | 9.2 ± .3 | 8.6 ± .3 | 8.6 ± .3 |
| 5 | 8.8 ± .6 | 9.1 ± .4 | 9.5 ± .3 | 9.9 ± .1 |
| 6 | 8.4 ± .4 | 9.5 ± .4 | 9.7 ± .2 | 10.3 ± .3 |
| 7 | 7.0 ± .8 | 8.6 ± .5 | 9.1 ± .4 | 9.0 ± .3 |
| 8 | 8.2 ± .8 | 7.7 ± .5 | 8.7 ± .4 | 8.2 ± .4 |

TABLE 3

Joint Inflammation Induced by Intra-Articular Antigen: Effect of Post-AIA Treatment with IL-1α and IL-1β (Joint Diam. in mm)

| Days After AIA | Treatment | | | |
|---|---|---|---|---|
| | IL-1α | IL-1β | Saline | GM-CSF |
| 0 | 4.8 ± .1 | 4.8 ± .1 | 4.8 ± .1 | 4.7 ± .1 |
| 1 | 7.4 ± .2 | 7.5 ± .1 | 6.9 ± .2 | 7.0 ± .2 |
| 2 | 8.0 ± .2 | 8.6 ± .2 | 7.8 ± .2 | 7.7 ± .1 |
| 5 | 9.1 ± .4 | 8.8 ± .3 | 10.4 ± .3 | 10.3 ± .3 |
| 6 | 8.5 ± .6 | 7.2 ± .3 | 9.8 ± .3 | 9.5 ± .2 |
| 7 | 8.0 ± .7 | 7.2 ± .4 | 10.2 ± .5 | 9.1 ± .4 |
| 8 | 8.2 ± .8 | 6.8 ± .6 | 9.4 ± .3 | 8.6 ± .4 |

FIG. 1 is a graph of the data presented in Table 3. FIG. 1 and Tables 2 and 3 suggest that joint inflammation caused by AIA can be reduced by pretreatment and post-treatment with IL-1α and IL-1β. IL-1β appears to provide a greater effect.

EXAMPLE 3

Evaluation of Dose-Response Relationship Between IL-1β Treatment and Reduction in AIA Joint Inflammation 20 rats were equally divided into four groups, designated Groups I, J, K and L. All 20 rats were immunized with 1 mg mBSA as described above, then treated with IA IL-1β or IA saline as follows.

Group I rats received right hind knee joint injections of saline on days 1, 7 and 14 following immunization. Group J rats received 10 ng IL-1β; Group K rats received 100 ng IL-1β; and Group L rats 1000 ng IL-1β, all in the right hind knee joint. The left hind knee joints of all 20 rats were injected with 10 μl saline.

On Day 21, all 20 rats received 100 μg mBSA in 10 μl saline in both right and left hind knee joints.

Figure 2:
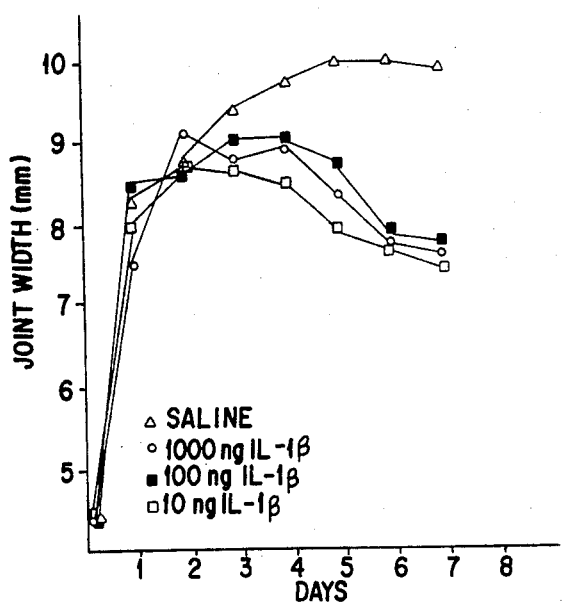
FIG. 2 is a graph showing the pretreatment effects of varying intra-articular dosages of IL-1β in ameliorating subsequent inflammation induced by intra-articular injections of mBSA in mBSA-immune rats.

The diameter of the largest region of the treated joints was then measured using a caliper. The results obtained are plotted in FIG. 2, and show approximately equivalent effects over the range of dosages selected.

What is claimed is:

1. A process for treating arthritis or inflammation comprising administering an effective amount of interleukin-1 (IL-1), in association with a pharmaceutical carrier, as an anti-arthritic or anti-inflammatory agent.

2. A process according to claim 1, wherein the IL-1 is IL-1α.

3. A process according to claim 2, wherein the IL-1 is human IL-1α.

4. A process according to claim 3, wherein the IL-1 is administered by injection.

5. A process according to claim 4, wherein the IL-1 is administered by intra-articular injection.

6. A process according to claim 1, wherein the IL-1 is IL-1β.

7. A process according to claim 6, wherein the IL-1 is human IL-1β.

8. A process according to claim 7, wherein the IL-1 is administered by injection.

9. A process according to claim 8, wherein the IL-1 is administered by intra-articular injection.

* * * * *